United States Patent [19]

Noiles

[11] Patent Number: 4,676,798
[45] Date of Patent: Jun. 30, 1987

[54] SOCKET BEARING ASSEMBLY FOR A CONSTRAINED BALL AND SOCKET JOINT

[75] Inventor: Douglas G. Noiles, New Canaan, Conn.

[73] Assignee: Joint Medical Products Corporation, Stamford, Conn.

[21] Appl. No.: 910,347

[22] Filed: Sep. 19, 1986

Related U.S. Application Data

[63] Continuation of Ser. No. 649,901, Sep. 12, 1984, abandoned.

[51] Int. Cl.$^4$ .............................................. A61F 2/34
[52] U.S. Cl. ...................................... 623/22; 623/19; 403/135
[58] Field of Search ....................... 623/16, 18, 20, 22, 623/23; 403/122, 133, 135

[56] References Cited

U.S. PATENT DOCUMENTS 3,226,141  12/1965  Sullivan, Jr. .......................... 403/135
3,863,273  2/1975   Averill .................................... 3/1 X
3,996,625  12/1976  Noiles .
4,410,295  10/1983  Ersoy et al. .......................... 403/135

FOREIGN PATENT DOCUMENTS

PCT/US84/-
00364  9/1984  PCT Int'l Appl. .

OTHER PUBLICATIONS

Richards Manufacturing Company, 2 page brochure, "Michael Reese Shoulder Prosthesis," 1980.

Primary Examiner—Richard J. Apley
Assistant Examiner—David Isabella
Attorney, Agent, or Firm—Maurice M. Klee

[57] ABSTRACT

A socket bearing assembly for a constrained ball and socket joint is provided which comprises: (a) a plastic socket bearing having a wall and a spherically-shaped cavity which has an opening defined by a rim for receiving the ball, the opening being smaller than the ball, and the wall having at least two cuts therethrough which extend from the rim towards the equator of the spherically-shaped cavity and which divide the portion of the wall in the vicinity of the opening into at least two flexible segments which can move apart to allow the ball to enter the cavity; (b) a reinforcing band; and (c) means associated with the bearing for attaching the band to the bearing at a location where the band can prevent the flexible segments from moving apart, thereby constraining the ball in the bearing. The bearing assembly is easily assembled in the operating room making it simpler for surgeons to use constrained ball and socket joints in both original and replacement implantations.

1 Claim, 12 Drawing Figures

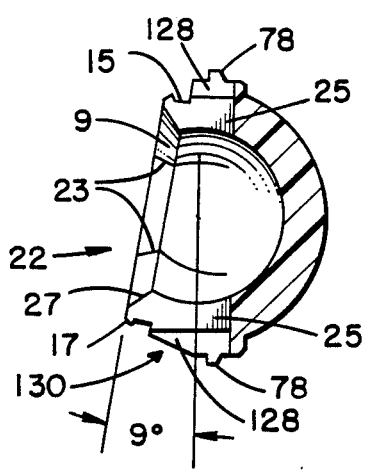
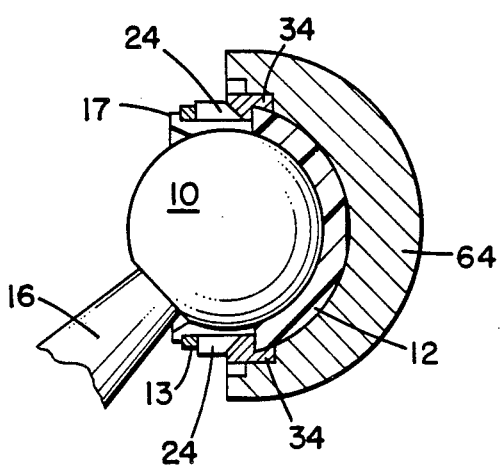
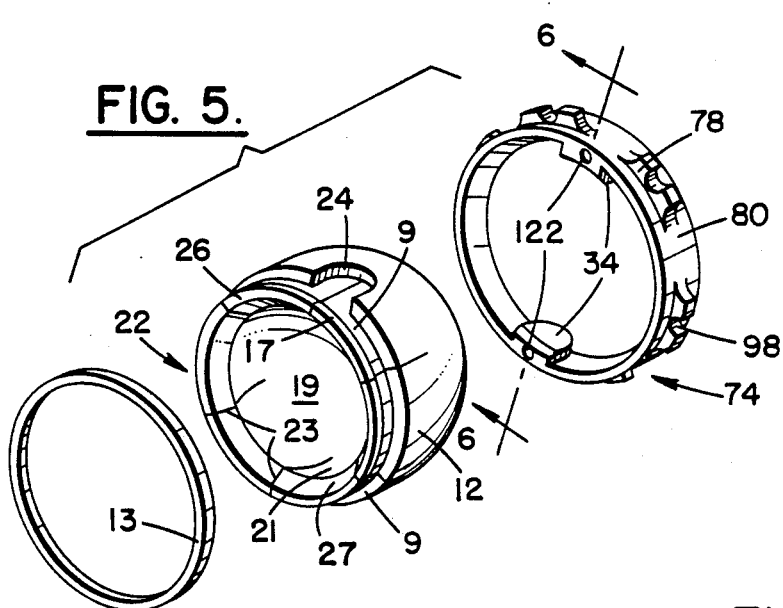
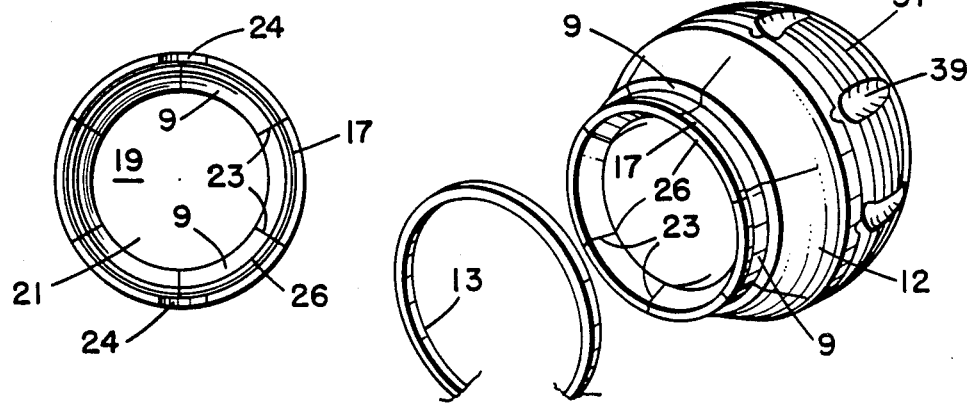

SOCKET BEARING ASSEMBLY FOR A CONSTRAINED BALL AND SOCKET JOINT

This is a continuation of co-pending application Ser. No. 649,901, filed on Sept. 12, 1984, now abandoned.

BACKGROUND OF THE INVENTION

1. Field of the Invention

This invention relates to artificial joints and in particular to artificial joints of the ball and socket type.

2. Description of the Prior Art

As is well known in the art, artificial hip and shoulder joints conventionally employ ball and socket articulations. The socket portion of the joint is attached to one bony structure, for example, the pelvis for a hip reconstruction. The ball is connected to an arm composed of a neck and a stem or shaft, and the stem or shaft is embedded in another bony structure, for example, the femur for a hip reconstruction.

A number of methods are known for retaining the ball in the socket. In the most common method, referred to herein as the "semi-constrained" construction, the patient's own anatomy, i.e., his muscles, tendons and ligaments, are used to retain the ball within the socket. For this construction, a hemispherical socket typically is used which allows the ball and its attached arm the maximum amount of movement without contact of the arm with the edge of the socket. The surgeon, when installing such a semi-constrained joint, aligns the ball and socket as closely as possible with the patient's natural anatomy so that the patient's movements do not tend to dislocate the ball from the joint.

In order to increase the inherent stability against dislocation of semi-constrained constructions, it has become conventional to add a cylindrical portion to the hemispherical socket to make it deeper. Although the ball is not physically constrained by the socket by this adjustment, the ball does have further to travel than if just a hemisphere had been used and thus some reduction in the propensity towards dislocation is achieved.

A recent study by the Mayo Clinic, which appeared in the December, 1982 edition of *The Journal of Bone and Joint Surgery*, reported a dislocation frequency of 3.2% for 10,500 hip joint implant procedures using the semi-constrained construction. Such dislocations essentially make the patient immobile and can necessitate a second operation. Because the success of semi-constrained constructions depends upon achieving a relatively precise alignment between the patient's anatomy and the components of the artificial joint and because a first operation and the healing process thereafter usually destroy or distort anatomical landmarks, even higher dislocation frequencies are encountered for second and subsequent implantations.

An alternative to the semi-constrained construction is the "constrained" construction wherein the ball is physically constrained within the socket. The present invention is directed to this type of construction.

In the constrained construction, a spherically-shaped bearing surrounds the ball and serves as the socket. The bearing is attached to a fixation element which is embedded in, for example, the patient's pelvic bone. The bearing encompasses more than one-half of the ball and thus constrains the ball and its attached arm from dislocation.

The bearing is made of metal or, more typically, of plastic, such as ultra-high molecular weight polyethylene (UHMWPE).

An example of a constrained construction using a metal socket bearing is shown in Noiles, U.S. Pat. No. Re. 28,895 (reissue of U.S. Pat. No. 3,848,272). In a practical sense, this joint can be said to be non-dislocatable. The force required to extract the metal sphere from the enclosing metal socket bearing is more than several thousand pounds. Accordingly, in use, rather than the metal ball dislocating from the metal socket bearing, any overly severe dislocating leverage will cause the fixation element to be disrupted from the bone in which it has been embedded.

Notwithstanding the fact that metal balls in metal socket bearings are non-dislocatable, they are used in only a minority of joint reconstructions because the medical profession is not in agreement that a metal sphere in a metal bearing is as biologically acceptable as a metal sphere in a UHMWPE plastic bearing, even though clinical use over 15 years has failed to show the metal to metal joint to be inferior to a metal to plastic joint.

In view of this prejudice against metal socket bearings, the constrained constructions in most common use today employ plastic bearings. For these constructions, a pre-assembled ball and socket bearing assembly is supplied to the surgeon. The manufacturer constructs the assembly by forcing the bearing over the ball. The more of the ball which is encompassed by the bearing, the greater the required assembly force, and the greater the constraining force to prevent post-operative dislocation of the joint. To aid in assembly, the socket bearings are usually heated to a non-destructive temperature (for example 70°-80° C. for UHMWPE). Plastic in general, and UHMWPE in particular, has a large coefficient of thermal expansion and such thermal expansion due to heating significantly aids in assembly.

An example of a constrained artificial joint employing a plastic bearing is shown in Noiles, U.S. Pat. No. 3,996,625. As can be seen in FIGURE 1 of this patent, a plastic bearing 17 fitted with a metal reinforcing band (un-numbered) extends beyond the diameter of ball 24 so as to physically constrain the ball within the bearing. The bearing itself is attached to fixation element 12. The metal reinforcing band is assembled over the lip of the opening of bearing 17 after that bearing has been forced over sphere 24. The reinforcing band increases the force required to dislocate the joint.

In practice, the design shown in FIGURE 1 of U.S. Pat. No. 3,996,625 has been found to resist direct dislocating forces of approximately five hundred pounds. Moreover, this joint has been found to suffer post-operative dislocations in fewer than 0.5% of the implantations performed. This is significantly better than the 3.2% dislocation frequency reported for semi-constrained constructions in the Mayo Clinic study discussed above.

Although highly successful, constrained ball and socket joints employing plastic socket bearings, including joints of the type shown in U.S. Pat. No. 3,996,625, have suffered from the disadvantage that unless they were designed to provide only a small constraining force, i.e., if they were designed to encompass only slightly more than half the ball, they could not conveniently be assembled in the operating room. Specifically, the force required to assemble the bearing onto the ball, even for a heated bearing, has in general been too great to be conveniently applied by a surgeon in the midst of a surgical procedure. Although mechanized assembly devices capable of generating the necessary force could have been used by surgeons, in practice, surgeons have preferred to use constrained joints where the socket bearing and ball have been pre-assembled.

The lack of a truely convenient way to assemble constrained joints in the operating room has limited the usefulness of these joints in the following ways. First, at the time of an initial joint implantation, the need to pre-assemble the socket bearing and the ball portion of the joint has meant that the surgeon has had to make the decision to employ a constrained joint prior to implantation of the ball's fixation element, e.g., prior to implantation of the stem or shaft portion of the arm attached to the ball. He could not postpone the decision as to the type of joint to use until after implantation of the fixation elements for both the ball and socket portions of the joint, when he might have had a fuller appreciation of the patient's medical condition and anatomy.

Similarly, if after an initial implantation, a patient proved to be particularly prone to dislocations with a semi-constrained construction, there has been no truly convenient way to change to a constrained construction employing a high-constraint plastic socket bearing without removing the ball portion of the original joint from the bone in which it had been originally implanted. Along these same lines, there has been no convenient way to replace a worn socket bearing of the constrained type without completely removing the entire ball portion of the joint from the patient.

SUMMARY OF THE INVENTION

In view of the above state of the art, it is an object of the present invention to provide a constrained ball and socket joint employing a plastic socket bearing which (1) provides a high level of constraining force for the ball, and (2) which can be easily assembled onto the ball at the surgical site. In particular, it is an object of the present invention to provide a constrained ball and socket joint which provides a level of constraint similar to that achieved by the joint shown in U.S. Pat. No. 3,996,625, and which can be easily assembled at the surgical site.

It is a further object of the invention to provide a constrained socket bearing assembly which can easily be assembled at the surgical site and used as the socket bearing portion of the ball and socket joints described in my copending and commonly assigned U.S. patent applications Ser. Nos. 473,431 and 553,520, filed Mar. 8, 1983, and Nov. 21, 1983, respectively.

To achieve these and other objects, the invention provides a socket bearing assembly for a constrained ball and socket joint comprising: (1) a plastic socket bearing having a wall and a spherically-shaped cavity which has an opening defined by a rim for receiving the ball, the opening being smaller than the ball, and the wall having at least two cuts therethrough which extend from the rim towards the equator of the spherically-shaped cavity and which divide the portion of the wall in the vicinity of the opening into at least two flexible segments which can move apart to allow the ball to enter the cavity; (2) a reinforcing band; and (3) means associated with the bearing for attaching the band to the bearing at a location where the band can prevent the flexible segments from moving apart, thereby constraining the ball in the bearing.

In the description of the preferred embodiments which appears below, the invention is described in the context of the ball and socket joints described in U.S. patent applications Ser. Nos. 473,431 and 553,520, referred to above, the pertinent portions of which are incorporated herein by reference. It is to be understood that the invention is also applicable to constrained ball and socket joints having other configurations now known or subsequently developed. It is also to be understood that both the foregoing general description and the following detailed description are explanatory only and are not restrictive of the invention.

The accompanying drawings, which are incorporated in and constitute part of the specification, illustrate the preferred embodiments of the invention, and together with the description, serve to explain the principles of the invention.

BRIEF DESCRIPTION OF THE DRAWINGS

FIG. 4 is a cross-sectional view of a socket bearing similar to the bearing of FIG. 1 but including a lip to help restrain dislocations of the assembled joint. The cross-section is taken in the same direction as cut lines 3—3 in FIG. 1.

FIG. 5 is an exploded view of an alternate socket bearing assembly constructed in accordance with the present invention wherein the bearing is allowed to rotate with respect to its fixation element so as to minimize the chance that the joint will dislocate during use.

FIG. 6 is a cross-sectional view along lines 6—6 in FIG. 5 showing an assembled joint using the socket bearing assembly of FIG. 5.

FIG. 7 is a plan view of the socket bearing of FIG. 5.

FIG. 8 is a perspective view of a socket bearing assembly constructed in accordance with the present invention and designed to be cemented directly to a prepared cavity in, for example, the patient's pelvic bone.

DESCRIPTION OF THE PREFERRED EMBODIMENTS

Figure 1:
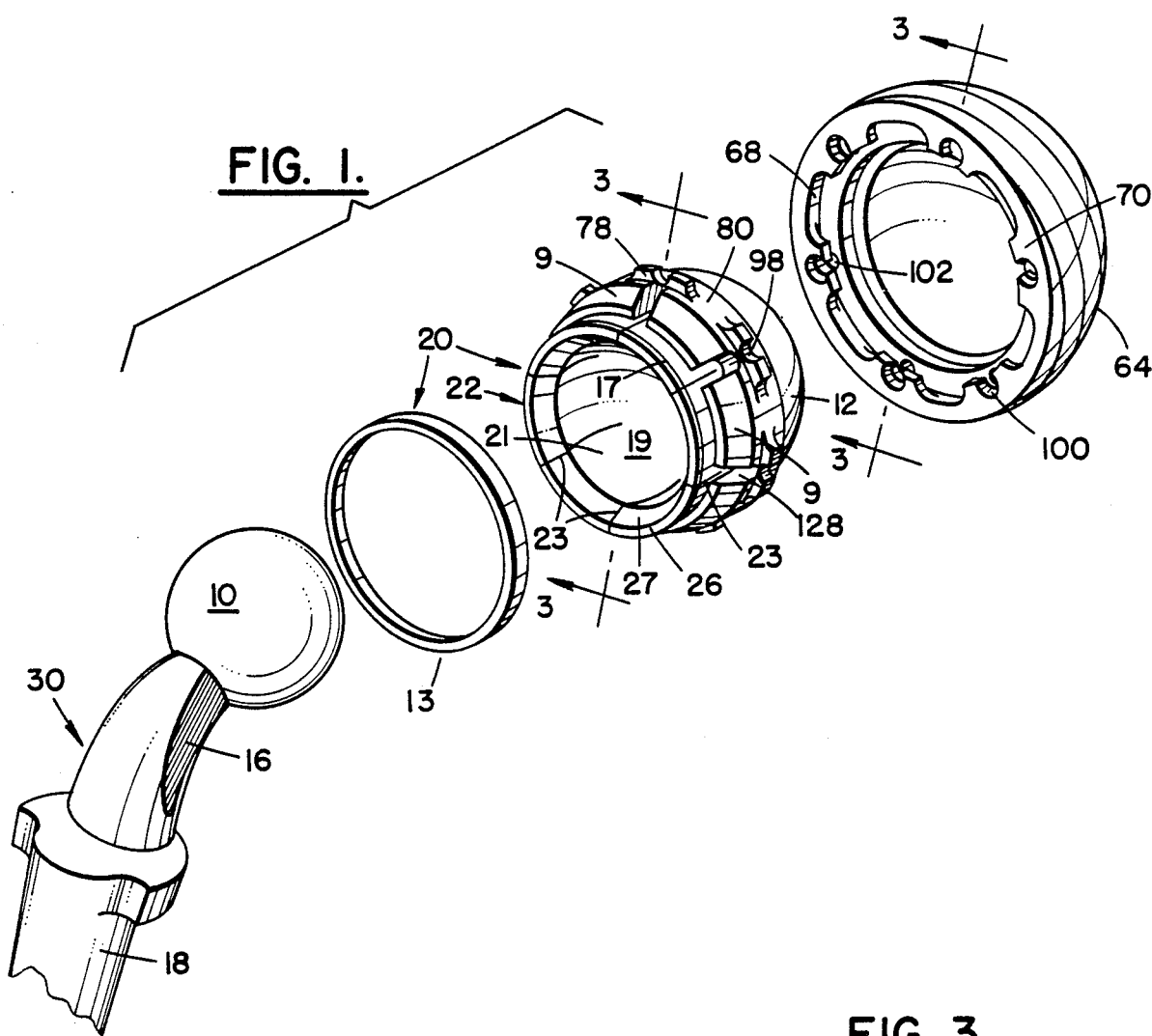
FIG. 1 is an exploded, perspective view of an artificial joint having a socket bearing assembly constructed in accordance with the present invention.
Figure 2:
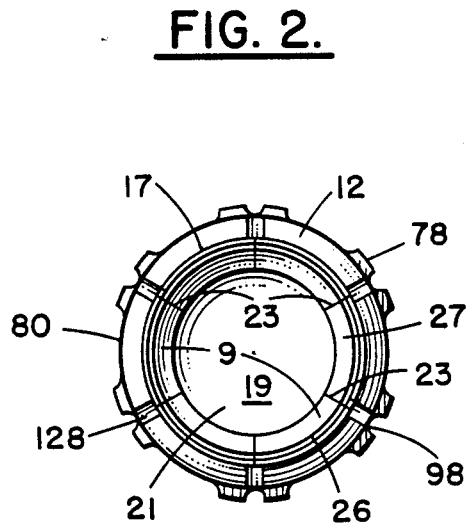
FIG. 2 is a plan view of the socket bearing of the joint of FIG. 1.
Figure 3:
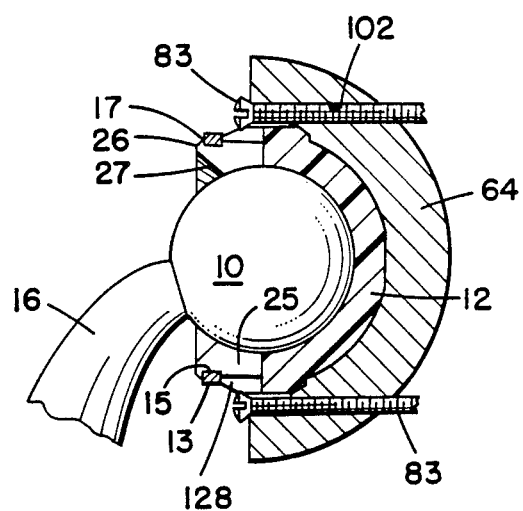
FIG. 3 is a cross-sectional view along lines 3—3 in FIG. 1 showing the joint of FIG. 1 in its assembled condition.

With reference now to the drawings, wherein like reference characters designate like or corresponding parts throughout the several views, there is shown in FIGS. 1-3 a ball and socket joint constructed in accordance with the present invention and comprising ball or sphere 10, fixation element 64, and socket bearing assemby 20, which consists of plastic socket bearing 12 and metal reinforcing band 13.

Figure 11:
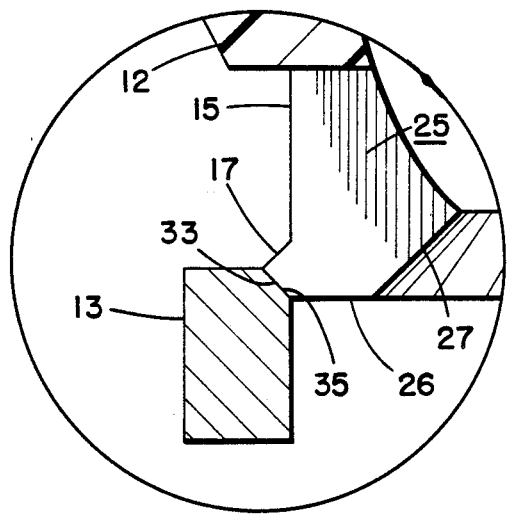
FIG. 11 is a front view, partially in section, illustrating the assembly of a reinforcing band onto a socket bearing by means of the instrument of FIG. 9.
Figure 11A:
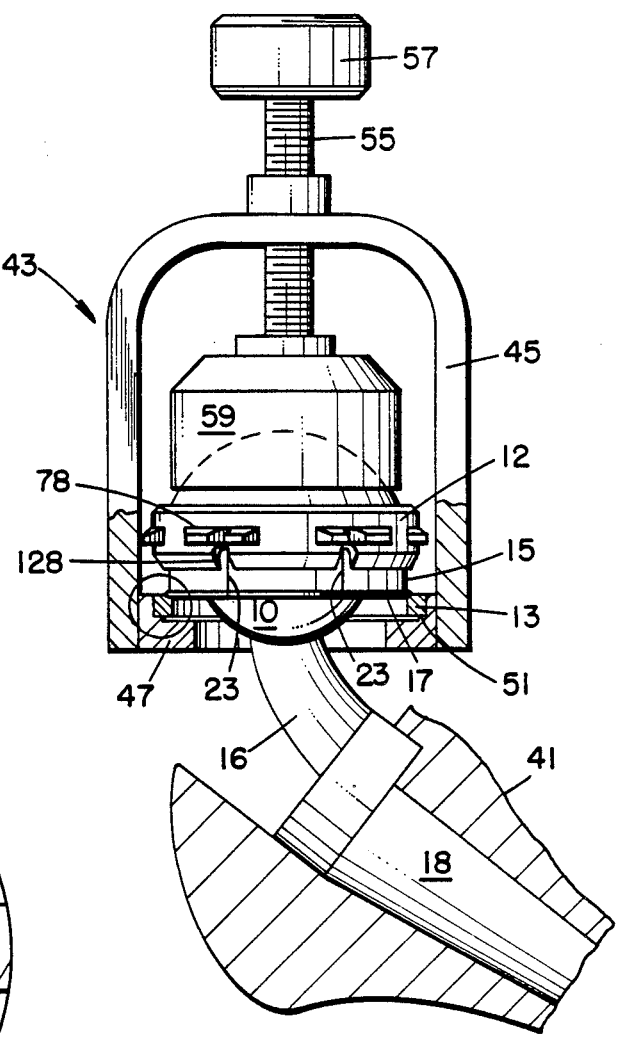
FIG. 11A is an enlarged, cross-sectional view of the circled portion of FIG. 11 showing the chamfers on the reinforcing band and the socket bearing which aid in guiding the band onto the bearing.

Reinforcing band 13 is attached to bearing 12 during assembly by means of recess 15 and lip 17 formed in the outer surface of the bearing (see, inter alia, Figure 11A). Ball 10 is attached to arm 30 which consists of neck 16 and stem or shaft 18, which stem or shaft is fixed to, for example, the femur bone at the time of implant surgery.

The metal components of the joint, e.g., fixation element 64, reinforcing band 13, ball 10, and arm 30 are made of surgically implantable metals and metal alloys which are compatible with one another. The preferred materials are titanium, titanium alloys, and cobalt-chromium-molybdenum alloys. If desired, other materials now known or subsequently developed can be used for these components. For example, reinforcing band 13 can be made of a stiff, plastic material, e.g., a reinforced plastic, which has a high modulus of elasticity.

Socket bearing 12 is made of plastic and preferably of ultra-high molecular weight polyethylene (UHMWPE). Inner spherical bearing surface 21 of bearing 12 defines a spherically-shaped cavity 19 for receiving ball 10. Ball 10 enters cavity 19 through opening 22 defined by rim 26. The smallest dimension of opening 22 is smaller than the diameter of ball 10 so that the ball will be constrained in socket bearing 12 once the joint has been assembled.

Extending from rim 26 towards the equator of cavity 19 are a plurality of cuts 23 which pass through wall 25 of bearing 12. The cuts divide the portion of wall 25 in the vicinity of opening 22 into a plurality of flexible, finger-like segments 9 which can move apart to allow ball 10 to enter cavity 19. This movement apart of segments 9 allows the forward portion of the bearing to expand over the ball during assembly and thus allows the ball and bearing to be assembled using force levels which can be conveniently applied in the operating room by surgeons or other medical personnel.

Reinforcing band 13, which when in place surrounds opening 22, prevents segments 9 from moving apart. This, in turn, prevents the front portion of the bearing from expanding around the ball and thus serves to constrain the ball in the bearing. With band 13 in place, it has been found that the application of a dislocating force to the ball results in segments 9 being forced together, rather than apart. As the dislocating force is increased, the segments continue to be forced together, with ultimate dislocation of the joint occurring through compression of the bearing material between the reinforcing band and the ball, rather than through segment separation.

Cuts 23 are easily formed in bearing 12 by applying a low level of steady pressure to a sharp knife, razor or similar device. The number and longitudinal lengths of the cuts will depend on the thickness of the bearing's wall, the type of plastic used, and the disparity between the size of opening 22 and the diameter of ball 10, as well as on the overall geometry of opening 22, e.g., on whether the opening includes an entrance ramp, such as ramp 27 shown in the figures.

For the bearing configurations shown in FIGS. 1-8 and for surgically implantable ultra-high molecular weight polyethylene (e.g., RCH-1000, Hoechst, West Germany), a wall thickness of approximately 5-10 mm, a ball diameter in the range of 22-32 mm, and a disparity of about 2 mm between the smallest dimension of opening 22 and the diameter of the ball, it has been found that two to six, and most preferably, four to six, symmetrically placed cuts which extend from rim 26 to about the level of the equator of cavity 19 work successfully. Cuts of this length and number have been found to not significantly decrease either the overall strength of the bearing or the constraining force which the bearing is capable of applying to the ball once reinforcing band 13 is in place. Similar cut configurations can be used for other bearing configurations, materials and dimensions, the specific number and length of cuts which are optimal for any particular configuration being readily determined by persons of ordinary skill in the art in view of the present disclosure.

The cut bearing/reinforcing band combination can be used with all types of constrained ball and socket joints which employ plastic socket bearings. By way of illustration, four possible configurations are shown in FIGS. 1-8. Three of these configurations (FIGS. 1-3, 4, and 5-7) can be used interchangeably with a common fixation element 64, while the fourth configuration (FIG. 8) is designed to be cemented directly to a prepared cavity in, for example, the patient's pelvic bone. It is to be understood, of course, that these four specific examples are not to be considered as limiting the invention in any way.

The interchangeable configurations of FIGS. 1-7 follow the teachings of my U.S. patent applications Ser. Nos. 473,431 and 553,520, referred to above. FIGS. 1-3 and 4 show two types of constrained joints employing stationary socket bearings, while FIGS. 5-7 show a constrained joint in which the socket bearing can rotate about an axis passing through the center of the ball. The bearings of FIGS. 1-3 and 4 differ in that the FIG. 1-3 bearing is symmetric, while that of FIG. 4 includes a lip 130 to further help restrain dislocations of ball 10 from bearing 12.

Lip 130 can be conveniently formed in bearing 12 by gradually sloping the front surface of the bearing as shown in FIG. 4. A suitable slope is on the order of 9°. Unlike the symmetric bearing of FIGS. 1-3, the bearing of FIG. 4 defines an orientation between itself and the patient's anatomy. Accordingly, when attaching this bearing to fixation element 64, the surgeon will orient the bearing so as to place lip 130 in the most advantageous position to inhibit dislocation.

The configuration of FIGS. 5-7 employs a bearing which can rotate about stub half pins 34 carried by bayonet ring 74. For this configuration, bearing 12 includes cylindrical surfaces 24 which engage stub pins 34 in the assembled joint. Although not shown in the figures, if desired, the range of rotation of bearing 12 about pins 34 can be limited by means of the polar pin system disclosed and claimed in copending and commonly assigned U.S. patent application Ser. No. 553,518 to Alfred Frederick DeCarlo, Jr., filed Nov. 21, 1983, the pertinent portions of which are incorporated herein by reference.

The use of a rotatable bearing increases the overall range of motion of the joint and thus further minimizes the chances of dislocation. Moreover, by properly orienting the bearing's axis of rotation with respect to the patient's anatomy, most of the highly repetitive load bearing motions of the joint can be made to occur by ball 10 rotating in bearing 12. With such an orientation, significant rotation of bearing 12 about stub pins 34 can be limited to relatively extreme motions of the joint, such as those needed to accommodate crossing the legs when seated in the case of hip joints. In this way, the joint can have the frictional characteristics of a small ball for most of the patient's motions, as is desirable, and yet the range of motion of a large ball, which clearly is also desirable.

The interchangeable configurations of FIGS. 1-7 are all designed to mate with fixation element 64. Preferably, the fixation element is constructed in accordance with the teachings of my copending and commonly assigned U.S. patent application Ser. No. 553,519, filed Nov. 21, 1983, the pertinent portions of which are incorporated herein by reference. Of course, if desired, fixation systems other than those of application Ser. No. 553,519, e.g., cemented systems, can be used to practice the present invention.

Each of the interchangeable configurations includes bayonet lugs and spaces 78 and 80 which are designed to mate with bayonet lugs and spaces 70 and 68 formed in fixation element 64. Assembly of the socket bearing to the fixation element is accomplished by simply inserting lugs 78 into spaces 68 in any of the several angular positions the bayonet lug fittings will permit. A fraction of a turn in either direction will engage lugs 78 under lugs 70, thus locking the bearing assembly to the fixation element. Alternatively, lugs 78 can be beveled at either their right or left hand leading edges so that insertion by rotation in only one direction is facilitated, e.g., clockwise rotation.

To aid in the rotation of bearing 12, the bearing can include slots 128 for engagement with a spanner wrench or the like. Similarly, for the embodiment of FIGS. 5-7, bayonet ring 74 can include apertures 122 for the same purpose. Once lugs 78 have been moved under lugs 70, the engagement between those lugs is secured by means of one or more screws 83 which pass through openings 100 and 98 in lugs 70 and 78, respectively, and then through holes 102 in fixation element 64 to engage the bone into which element 64 has been implanted by the surgeon.

As an alternative to the use of a separate fixation element, FIG. 8 illustrates a constrained socket bearing assembly designed to be cemented directly into a prepared cavity in, for example, the patient's pelvic bone. The outside surface of bearing 12 includes a series of grooves 37 and slots 39 to aid in forming a strong bond between the prosthesis and the cement (e.g., surgically implantable polymethyl methacrylate) used to attach the prosthesis to the patient's bone.

A typical sequence of steps for implanting the prosthesis of FIGS. 1-3 is as follows. Stem 18 of arm 30 is implanted by conventional techniques in, for example, the patient's femur bone 41 (see FIGS. 10-11). Fixation element 64 can also be implanted by conventional techniques, or, most preferably, by the techniques described in my above-referenced copending application Ser. No. 553,519.

To assemble bearing 12 onto ball 10, reinforcing band 13 is first placed over the ball, and then by means of flexible segments 9, bearing 12 is pushed onto the ball. It has been found that the assembly can be easily done by hand when between four and six cuts 23 have been made through the front portion of the bearing. Alternatively, as described in detail below, an assembly instrument of the type shown in FIGS. 9-11 can be used to push the bearing onto the ball.

Once the bearing is on the ball, reinforcing band 13 is pushed over lip 17 and into recess 15 formed in the outer surface of the bearing. To aid in this assembly process, band 13 and lip 17 include complementary chamfers 33 and 35, respectively, which help guide the band onto the bearing (see FIG. 11A). As with the assembly of the bearing onto the ball, the assembly of the band onto the bearing can be done completely by hand or, if desired, with the aid of the assembly instrument of FIGS. 9-11.

Once the bearing and reinforcing band have been assembled onto the ball, the bearing is inserted into fixation element 64 in any of the several angular positions the bayonet lug fittings will permit. Using a spanner wrench inserted into slots 128, the bearing is then turned in either direction to engage lugs 78 under lugs 70. Alternatively, as discussed above, lugs 78 can be beveled at either their right or left hand leading edges so that insertion by rotation in only one direction is facilitated, e.g., clockwise rotation. Assembly of the joint is completed by locking bayonet lugs 78 and 70 in place by means of one or more screws 83 which pass through openings 100 and 98 in lugs 70 and 78, respectively, and then through holes 102 to engage the bone into which fixation element 64 has been implanted.

The embodiments shown in FIGS. 4-8 are implanted in essentially the same manner as the FIGS. 1-3 embodiment. The FIG. 4 embodiment includes the extra step of orienting the bearing so as to place lip 130 in the most advantageous position to inhibit dislocation. The FIGS. 5-7 embodiment also includes an orientation step, in this case to align the the axis of rotation of the bearing with respect to the patient's anatomy so that most of the highly repetitive load bearing motions of the joint will occur by ball 10 rotating in bearing 12. Also, for this embodiment, bayonet ring 74 is assembled onto bearing 12 before the bearing is assembled onto the ball. For the embodiment of FIG. 8, bearing 12 will in most cases be cemented in place prior to assembling the bearing onto the ball, although, if desired, the bearing and ball can be assembled first, and that combination then cemented in place.

Figure 9:
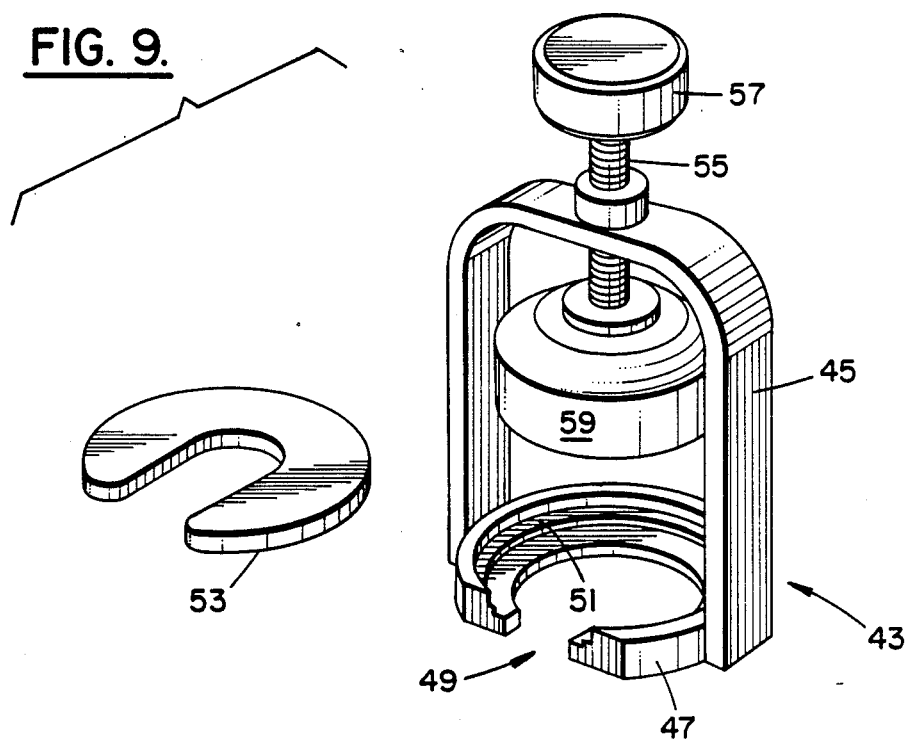
FIG. 9 is a perspective view of an instrument suitable for use in an operating room to assemble the components of the socket bearing assembly of the present invention.
Figure 10:
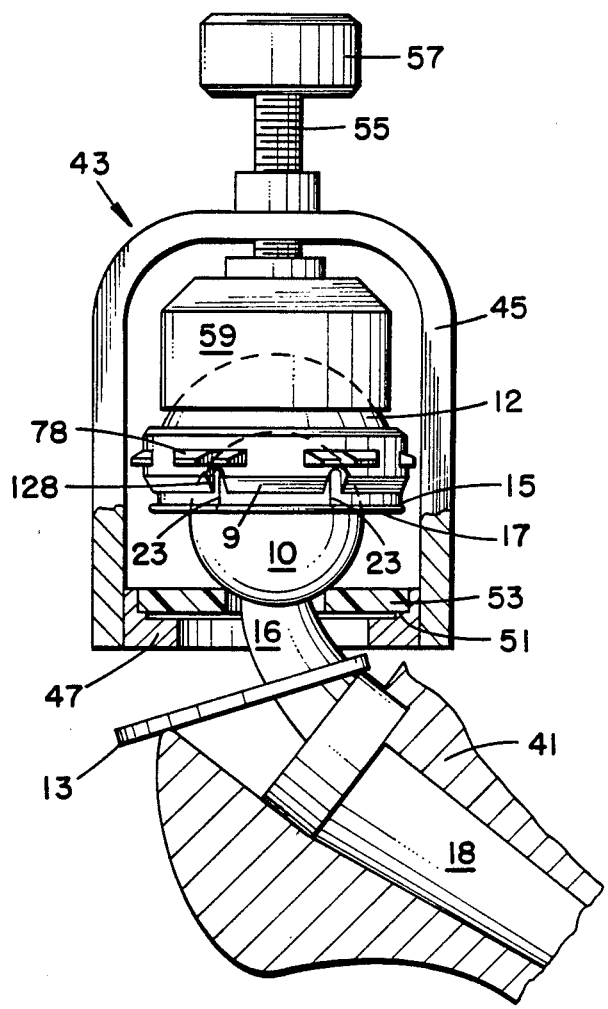
FIG. 10 is a front view, partially in section, illustrating the assembly of a socket bearing onto a ball by means of the instrument of FIG. 9.

To aid in the assembly process, an instrument or tool, such as instrument 43 illustrated in FIGS. 9-11, can be used with the socket bearing assembly of the present invention. Instrument 43 includes a frame 45 to which is attached threaded screw 55 having knob 57 at one end and dome 59 at the other end, the dome being sized to engage the outer surface of bearing 12. Attached to the bottom portion of frame 45 is C-shaped base 47 having an opening 49 sized to fit around neck 16 of the ball portion of the joint. C-shaped base 47 includes a seat 51 which receives C-shaped washer 53 during the assembly of the bearing onto the ball (see FIG. 10), and which receives reinforcing band 13 during the assembly of the reinforcing band onto the bearing (see FIG. 11). C-shaped washer 53 is sized to engage the bottom of ball 10 so that the turning of threaded screw 55 by means of knob 57 will force bearing 12 onto the ball.

As shown in FIG. 10, to assemble the bearing onto the ball, band 13 is placed over ball 10, instrument 43 is placed about the ball with C-shaped washer 53 engaging the bottom of the ball, and knob 57 is turned until dome 59 forces bearing 12 onto the ball by means of flexible segments 9. Knob 57 is then turned in the opposite direction so that the instrument can be removed from the ball/bearing assembly and the C-shaped washer 53 removed from the instrument.

Assembly of band 13 onto the bearing is illustrated in FIG. 11. Instrument 43 is reapplied to the ball/bearing assembly with band 13 in seat 51, instead of C-shaped washer 53. Knob 57 is turned until dome 59 forces the band onto the bearing. Chamfers 33 and 35 on the band and the bearing, respectively, help guide the band onto the bearing during this process. Once the band is in place, knob 57 is turned in the opposite direction and the instrument is removed from the ball/bearing/band assembly.

In addition to using an instrument to help assemble the bearing onto the ball, assembly can also be aided by heating the bearing to a non-destructive temperature (e.g., 70°-80° C. for UHMWPE) before the bearing and the ball are combined. Such heating will cause the bearing to expand and thus will decrease the disparity between the size of opening 22 and the diameter of the ball. Heating can be used with both hand assembly and instrument assisted assembly.

The assembly procedures described above are applicable both to original implantations and to subsequent implantations designed, for example, to replace a worn bearing or to substitute a constrained construction for a semi-constrained construction.

In the case of subsequent implantations, the ability to assemble the socket bearing assembly of the present invention at the surgical site and the fact that the assembly can be applied to the ball after the ball has been implanted, means that the existing ball of the patient's old prosthesis need not be disturbed to use the present invention. This is so irrespective of the particular manufacturer of the ball portion of the joint. That is, the present assembly can be used universally and is not limited to existing joints having a particular construction.

The ability to implant the highly constrained socket bearing assembly of the present invention without removing the patient's existing ball is an important improvement over the prior art wherein the surgeon's only option was basically to start over from the beginning and re-implant both a new ball and a new socket. Moreover, if the patient's existing prosthesis was designed to accept socket bearings having a variety of configurations, i.e., if the existing prosthesis was designed in accordance with my copending applications Ser. Nos. 473,431 and 553,520, even less disturbance of the existing joint is required. For example, for a fixation element 64 of the type shown in FIG. 1, substitution of a new bearing assembly only requires removing the threaded screws 83 which were used to lock the old bearing in place. Clearly, the ability to construct a highly constrained prosthesis with such minimal disturbance of the patient's existing prosthesis is of great value to both the surgeon and the patient.

Numerous modifications and variations of the present invention are possible in light of the above teachings. For example, reinforcing band 13 can have a variety of shapes other than that illustrated in the figures, and the band can be retained on bearing 12 using fastening means of various types. Similarly, socket bearings having configurations other than those specifically illustrated herein can be used in the practice of the invention. It is therefore understood that within the scope of the appended claims, the invention may be practiced otherwise than as specifically described.

What is claimed is:

1. A constrained ball and socket joint for implantation in a patient's body comprising a ball portion and a socket portion, the ball portion including:
 (a) a ball; and
 (b) first fixation means for implantation in a first bony structure, said fixation means being connected to said ball; and the socket portion including:
 (a) second fixation means for implantation in a second bony structure, said fixation means being in the form of a cup;
 (b) a socket bearing assembly for installation in said second fixation means including:
  (i) a surgically implantable, one-piece, plastic socket bearing having a wall and a spherically-shaped cavity which envelopes more than a hemisphere and which has an opening defined by a rim for receiving the ball, the opening being smaller than the ball, and the wall having at least two cuts therethrough which extend from the rim towards the equator of the spherically-shaped cavity and which divide the portion of the wall in the vicinity of the opening into at least two flexible segments which can move apart to allow the ball to enter the cavity, said cuts in the socket bearing being fully closed except when the ball is entering the cavity and said cuts being formed using a thin cutting instrument so that essentially no material is removed from the socket bearing in the region of the cuts;
  (ii) a reinforcing band which is placed over the ball before the ball is assembled into the bearing; and
  (iii) means associated with the bearing for attaching the band to the bearing at a location where the band can prevent the flexible segments from moving apart, thereby constraining the ball in the bearing; and
 (c) connecting means associated with the socket bearing and with the cup-shaped second fixation means for releasably connecting the bearing to said means, a portion of the bearing extending beyond the face of the cup when the bearing is connected to the cup, the reinforcing band being separate from the connecting means and being attached to the portion of the bearing which extends beyond the cup;

the portion of the ball which is enveloped by the socket bearing in the assembled joint being more than a hemisphere whereby the ball is constrained in the bearing such that the application of a dislocating force to the ball results in the flexible segments being forced together, rather than apart, with ultimate dislocation of the joint occurring through compression of the plastic bearing material between the reinforcing band and the ball in a manner to close the at least two cuts, rather than through separation of the segments from one another.

* * * * *